United States Patent [19]

Joly et al.

[11] 4,296,091
[45] Oct. 20, 1981

[54] NOVEL SYNERGISTIC INSECTICIDES

[75] Inventors: Robert Joly, Montmorency; Charles Pavan, Nogent-sur-Marn; Pierre R. Carle, Rognonas, all of France

[73] Assignee: Roussel Uclaf, Paris, France

[21] Appl. No.: 128,461

[22] Filed: Mar. 10, 1980

[30] Foreign Application Priority Data

Mar. 16, 1979 [FR] France .................... 79 06712

[51] Int. Cl.³ .............. A01N 25/00; A01N 37/00; A01N 37/08; A01N 25/06
[52] U.S. Cl. ........................................ 424/18; 424/16; 424/27; 424/40; 424/306
[58] Field of Search ................ 424/304, 324, 306, 16, 424/18, 27, 40

[56] References Cited

U.S. PATENT DOCUMENTS

| | | | |
|---|---|---|---|
| 3,911,101 | 10/1975 | Okuno | 424/40 |
| 3,934,023 | 1/1976 | Okuno et al. | 424/274 |
| 3,973,036 | 8/1976 | Hirano et al. | 424/304 |
| 4,100,297 | 7/1978 | Grandadam et al. | 424/304 |

FOREIGN PATENT DOCUMENTS 5826 12/1979 European Pat. Off. ............ 424/304

*Primary Examiner*—Douglas W. Robinson
*Attorney, Agent, or Firm*—Hammond & Littell, Weissenberger and Muserlian

[57] ABSTRACT

Novel synergistic insecticidal compositions comprising as the active ingredient an insecticidally effective amount of a synergistic mixture of 90 to 60% by weight of (S) 1-oxo-2-allyl-3-methyl-cyclopent-2-en-4-yl d trans chrysanthemate and 10 to 40% by weight of (R) 1-oxo-2-allyl-3-methyl-cyclopent-2-en-4-yl d trans chrysanthemate and to a novel method of combatting arthropodes.

17 Claims, No Drawings

NOVEL SYNERGISTIC INSECTICIDES

OBJECT OF THE INVENTION

It is an object of the invention to provide novel synergistic compositions for combatting arthropodes.

It is another object of the invention to provide a novel method of combatting arthropodes.

These and other objects and advantages of the invention will become obvious from the following detailed description.

THE INVENTION

The novel compositions of the invention are comprised of a pesticidal compositions containing as the active ingredient an insecticidally effective amount of a synergistic mixture of 90 to 60% by weight of (S) 1-oxo-2-allyl-3-methylcyclopent-2-en-4-yl d trans chrysanthemate and 10 to 40% by weight of (R) 1-oxo-2-allyl-3-methyl-cyclopent-2-en-4-yl d trans chrysanthemate. Preferably, the compositions contain 80 to 70% of the (S) ester and 20 to 30% of the (R) ester and most preferably about 75% by weight of the (S) ester and about 25% by weight of the (R) ester, the latter being preferred to herein after as Esbiothrine.

The compositions may be in any of the usual form of pesticidal compositions such as solutions, emulsion, aerosol sprays and the like but are preferably used in the form of a fumigant wherein the active ingredient is vaporized. One such form has the non-active part of the fumigant as a combustible insecticidal serpentine or coil and another form has the non-active part of the fumigant as an incombustible fibrous substrate and after incorporation of the active ingredient, the fumigant is put in a heating apparatus such as an electric mosquito destroyer whereby the active ingredients may be vaporized at will for prolonged periods of time. In the latter case, the amount of active ingredient may be, for example, 0.03 to 95% by weight.

In the case of serpentine insecticides, the inert combustible support material may be made of pyrethrum residue, Tabu powder (or powder of *Machilus Thumbergii* leaves), pyrethrum stalk powder, powder of cedar-tree leaves, sawdust such as pine sawdust, starch and shells powders such as powdered cocoanut shells. In this instance, the amount of active material in the serpentine may be 0.03 to 1.0% by weight.

The compositions may also be prepared in the form of a sprayable oil as a base for the active composition in which the oil is used impregnate the wick of a lamp and which is capable of burning to vaporize the active compositions. In this case, the concentration of the active ingredient is preferably 0.03 to 95% by weight. The compositions may also be in the form of aerosol sprays by incorporating the active composition into the necessary adjuvants or in any other suitable form to diffuse the active composition.

The compositions can also have incorporated therein other usual ingredients such as stabilizers such as phenols and arylamines, classical synergists of pyrethrinoids such as 1-(2,5,8-trioxadodecyl-2-propyl-4,5-methylenedioxy)-benzene or piperonyl butoxide, N-(2-ethyl-heptyl)-bicyclo-[2,2,1]-5-hepten-2,3-dicarboximide and piperonyl-bis-2-(2'-n-butoxyethoxy)-ethyl acetal or Tropital, antioxidants such as tocopherol acetate or emulsifying agents.

The compositions of the invention may be used in the home to destroy insects such as houseflies, mosquitoes, etc. and in industrial locations for destroying, for example, insect pests for cereal crops and insect pests for horticulture. The compositions may also be used in the veterinary field to combut sarcoptides and ixodides, especially gales and ticks. In the latter field, the active compositions and the other additions are generally used in solution in an alcohol or mixture of alcohols.

The synergistic mixtures of the invention may be prepared by homogenizing in suitable volume proportions S-bioallethrine (S-allethrolone d trans chrysanthemate) and R-bioallethrine (R-allethrolone d trans crysanthemate). The said two esters may be prepared by classical methods for esterifying R-allethrolone of S-allethrolone with d trans chrysanthemic acid. The said allethrolones may be prepared, for example, by the process of French Pat. No. 2,355,815 and No. 2,362,830.

The synergistic activity of the claimed compositions has been demonstrated on houseflies, Aedes aegypti and Culex pipiens by comparative tests with Esbiothrine, Bioallethrine which is R,S-allethrolone d trans chrysanthemate and S-Bioallethrine which is (S) allethrolone d trans chrysanthemate. The relative power of the said compositions was determined by the rats.

$$RP = \frac{\text{activity of } A}{\text{activity of } B}$$

R-bioallethrine is known to have a negligible insecticidal activity and was therefore not included in the tests.

The experimental data presented infra shows clearly the superior insecticidal activity of the compositions of the invention. For example, the relative power of Esbiothrine which is a mixture of 75% by S-bioallethrine and about 25% R-bioallethrine with respect to bioallethrine would be expected to be 75/50 or 1.5 while the experimental test showed a relative power of 2 to 2.5 which clearly shows the synergistic activity of the compositions of the invention.

The novel method of the invention for combatting arthropodes comprises contacting arthropodes with a lethal amount of an insecticidally effective amount of a synergistic mixture of 90 to 60% by weight of (S) 1-oxo-2-allyl-3-methylcyclopent-2-en-4-yl d trans chrysanthemate and 10 to 40% by weight of (R) 1-oxo-2-allyl-3-methyl-cyclopent-2- en-4-yl d trans chrysanthemate.

In the following examples there are described several preferred embodiments to illustrate the invention. However, it is to be understood that the invention is not intended to be limited to the specific embodiments.

EXAMPLE 1

A serpentine fumigant or coil was prepared containing 40 g of Tabu powder 35 g of cocoa nut powder, 10 g of pinewood sawdust, 12.4 g of starch, 0.5 g of perfume, 1.3 g of salicylanilide and 0.8 g of Esbiothrine.

EXAMPLE 2

An aerosol preparation was prepared containing 0.2% by weight of Esbiothrine, 19.8% by weight of an emulsion and 80% by weight of Freon.

EXAMPLE 3

An insecticidal composition for an electrical heater was prepared by adsorbing a solution of 0.6 g of Esbiothrine in 5 ml of toluene onto the surface of a piece of a parallelepipedic inert fibrous material measuring 2×2×0.8 cm and a second piece of the same dimensions fixed to said first piece to obtain a fumigant composition which could be used for heating on a plate provided with electrical resistance.

EXAMPLE 4

A veterinary composition was prepared containing 5 g of Esbiothrine, 25 g of piperonyl butoxide, 10 g of Polysorbate 80, 25 g of Triton X 100, 1 g of tocopherol acetate and sufficient ethanol for 100 ml of solution.

INSECTICIDAL STUDY

The synergistic insecticidal activity of the mixture of the invention indicated as Esbiothrine is shown by the following tests.

A. Tests on Domestic Musca

Neutral coils were impregnated with an acetone solution of the test products by depositing from a pipette on their two faces using 1.5 to 2 per gram of the coil. The test was effected in a transparent glass cube measuring 70 mm per edge with 20 female domestic flies per test about 4 to 5 days old. After a few minutes, a piece of the coil weighing about 2 g was introduced into a central trap secured at a lower face of the cube and the coil was burned at both ends. The burning of the coil lasted for the length of the test or until 95% of the flies were knocked down (K.D.). The test was repeated 3 times for each dose. The known down controls were effected all the minutes.

5 minutes after the end of the burning, the enclosure was ventilated and the insects were regrouped in cylindrical cages (OMS model) provided with a piece of damp cotton to ensure the survival of any eventually recuperating insects. The insects were then stored in a climatized room at 22° C.±1° and a 65%±5% relative humidity and the degree of apparent mortality (killing time or KT) was determined after 24 hours and the results are reported in the following Tables.

TABLE I

| PRODUCTS | Doses in % | Average of KT 50 | Average of KT 90 | % Mortality After 24 h | Combustion Rate Coil in mg/mn |
|---|---|---|---|---|---|
| Bioallethrine | 0.15 | 19.3 | 25.3 | 1.7 | 68.4 |
|  | 0.30 | 15.3 | 19.8 | 8.3 | 73.8 |
| (50% R + | 0.45 | 14.2 | 18.5 | 1.7 | 71.3 |
| 50% S) | 0.60 | 12.9 | 16.7 | 1.7 | 69.9 |
| S-Bioallethrine | 0.075 | 23.7 | 33.7 | 0 | 69.7 |
|  | 0.15 | 16.8 | 21.8 | 5 | 69.5 |
| (100% S) | 0.30 | 12.6 | 15.7 | 1.7 | 72.6 |
|  | 0.45 | 11.0 | 14.8 | 5 | 71.5 |
| Esbiothrine | 0.075 | 21.8 | 31.3 | 1.7 | 68.6 |
|  | 0.15 | 14.8 | 19.5 | 1.7 | 73.1 |
| (75% S + | 0.30 | 12.1 | 16.8 | 8.3 | 72.8 |
| 25% R) | 0.45 | 10.8 | 14.7 | 3.3 | 71.5 |

The results of Table I were used to establish Tables II and III.

TABLE II

| | Concentrations (C) and Relative Power (RP) in KT 50: | | | | | | | |
|---|---|---|---|---|---|---|---|---|
| | 11.5 min. | | 13 min. | | | 14.5 min. | | |
| PRODUCTS | C | R.P. | C | R.P. | | C | R.P. | |
| Bioallethrine | — | — | 0.600 | 1 | | 0.390 | 1 | |
| S-Bioallethrine | 0.395 | 1 | 0.295 | 2.03 | 1 | 0.220 | 1.77 | 1 |
| Esbiothrine | 0.365 | 1.08 | 0.240 | 2.50 | 1.23 | 0.160 | 2.44 | 1.38 |

TABLE III

| | Concentrations (C) and Relative Power (RP) in KT 90: | | | | | | | |
|---|---|---|---|---|---|---|---|---|
| | 17 min. | | 18 min. | | | 19 min. | | |
| PRODUCTS | C | R.P. | C | R.P. | | C | R.P. | |
| Bioallethrine | 0.580 | 1 | 0.48 | 1 | | 0.37 | 1 | |
| S-Bioallethrine | 0.275 | 2.11 | 1 | 0.24 | 1.96 | 1 | 0.205 | 1.81 | 1 |
| Esbiothrine | 0.275 | 2.11 | 1.0 | 0.22 | 2.14 | 1.09 | 0.175 | 2.11 | 1.17 |

B. Test against *Culex pipiens*

The test was analogous to Test A on flies and the Culex were 2 to 3 days old. The piece of coil introduced in the trap weighed about 1 g and was burned at two ends. The degree of KD was determined in 30 seconds and the results are reported in the following Tables.

TABLE IV

| PRODUCTS | Doses in % | Average of KT 50 | Average of KT 90 | % of Mortality After 24 h | Rate of combustion of coil in mg/mm |
|---|---|---|---|---|---|
| Bioallethrine | 0.15 | 7.8 | 9.3 | 60.6 | 72.5 |
|  | 0.30 | 6.2 | 7.4 | 72.8 | 75.3 |
|  | 0.45 | 5.3 | 6.6 | 78.3 | 75.7 |
| S-Bioallethrine | 0.075 | 7.6 | 9.5 | 45.3 | 75.8 |
|  | 0.15 | 6.2 | 8.1 | 68.3 | 76.7 |
|  | 0.30 | 4.7 | 6.1 | 87.3 | 72.5 |
| Esbiothrine | 0.075 | 7.3 | 8.7 | 57.3 | 76.6 |
|  | 0.15 | 6.1 | 7.6 | 73.1 | 73.8 |
|  | 0.30 | 4.8 | 6.3 | 88.6 | 74.7 |

The results of Table IV were used to establish Tables V and VI.

TABLE V

| | Concentrations (C) and Relative power (RP) of KT 50 | | | | | | | |
|---|---|---|---|---|---|---|---|---|
| | 5.5 min. | | 6.25 min. | | | 7.0 min. | | |
| PRODUCTS | C | R.P. | C | R.P. | | C | R.P. | |
| Bioallethrine | 0.410 | 1 | 0.295 | 1 | | 0.210 | 1 | |
| S-Bioallethrine | 0.205 | 2.00 | 1 | 0.145 | 2.03 | 1 | 0.102 | 2.06 | 1 |
| Esbiothrine | 0.205 | 2.00 | 1.00 | 0.135 | 2.19 | 1.07 | 0.088 | 2.39 | 1.16 |

TABLE VI

| PRODUCTS | Concentrations (C) and Relative power (RP) of KT 90 | | | | | | | | |
|---|---|---|---|---|---|---|---|---|---|
| | 7 min. | | | 7.75 min. | | | 8.5 min. | | |
| | C | R.P. | | C | R.P. | | C | R.P. | |
| Bioallethrine | 0.37 | 1 | | 0.27 | 1 | | 0.20 | 1 | |
| S-Bioallethrine | 0.22 | 1.68 | 1 | 0.16 | 1.69 | 1 | 0.118 | 1.70 | 1 |
| Esbiothrine | 0.205 | 1.81 | 1.07 | 0.135 | 2.0 | 1.19 | 0.086 | 2.33 | 1.37 |

C. Tests against *Aedes aegypti*

The test procedures was the same as that of Test B using one g of coil burned at one end only and the results are reported in the following Tables.

TABLE VII

| PRODUCTS | Doses in % | Average of KT 50 | Average of KT 90 | % of Mortality after 24 h | Rate of combustion of coil in mg/mn |
|---|---|---|---|---|---|
| Bioallethrine | 0.0375 | 18.3 | 21.7 | 30 | 35.4 |
| | 0.075 | 9.0 | 11.2 | 46.7 | 38.5 |
| | 0.150 | 7.6 | 9.7 | 80 | 38.3 |
| S-Bioallethrine | 0.0375 | 12.5 | 15.8 | 51.7 | 35.6 |
| | 0.075 | 7.4 | 9.0 | 70.0 | 40.0 |
| | 0.150 | 6.0 | 7.7 | 95.0 | 43.5 |
| Esbiothrine | 0.0375 | 12.3 | 15.3 | 48.3 | 36.9 |
| | 0.075 | 6.7 | 8.8 | 93.3 | 42.0 |
| | 0.150 | 5.0 | 6.3 | 96.7 | 41.5 |

The results of Table VII were used to establish Tables VIII and IX

TABLE VIII

| PRODUCTS | Concentrations (C) and Relative power (RP) of KT 50 | | | | | |
|---|---|---|---|---|---|---|
| | 5.5 min. | | 6.5 min. | | 7.5 min. | |
| | C | R.P. | C | R.P. | C | R.P. |
| Bioallethrine | — | — | — | — | 0.155 | 1 |
| S-Bioallethrine | 0.190 | 1 | 0.115 | 1 | 0.070 | 2.21 |
| Esbiothrine | 0.120 | 1.58 | 0.080 | 1.44 | | |

TABLE IX

| PRODUCTS | Concentrations (C) and Relative power (RP) of KT 90 | | | | | | |
|---|---|---|---|---|---|---|---|
| | 8.0 min. | | 8.5 min. | | 9.0 min. | | |
| | C | R.P. | C | R.P. | C | R.P. | |
| Bioallethrine | — | — | — | — | 0.20 | 1 | |
| S-Bioallethrine | 0.125 | 1 | 0.097 | 1 | 0.075 | 2.67 | 1 |
| Esbiothrine | 0.092 | 1.36 | 0.080 | 1.21 | | | |

GENERAL CONCLUSIONS

If the insecticidal activity was strictly proportioned to the content of the S isomer, in calculating the relative power of Bioallethrine, S-Bioallethrine and Esbiothrine as a function of proportions of S-Bioallethrine contained in the 3 products, the expected R.P. results would be: R.P. 2 for S-bioallethrine/Bioallethrine, 1.5 for Esbiothrine/Bioallethrine and 0.75 for Esbiothrine/S-Bioallethrine.

However, the experimental results can be summerized as follows:

S-Bioallethrine/Bioallethrine—RP of 2 for $KT_{50}$ and $KT_{90}$ against flies, Culex and Aedes.

Esbiothrine/Bioallethrine—RP for $KT_{50}$, the RP was 2.3 to 2.50 for flies and near 2 for Culex and for $KT_{90}$, the RP was 2 for flies and Culex.

Esbiothrine/S-Bioallethrine—for $KT_{50}$, the RP was 1 for flies and Culex and 1.5 for Aedes and for $KT_{90}$, the RP was slightly greater than 1 for flies and Culex and 1.30 for Aedes.

This means that the relative power values obtained experimentally conforms generally with that predicted for the Esbiothrine/S-Bioallethrine relationship (RP is 2). Contrary to that drawn from the Esbiothrine/S-Bioallethrine relationship (RP is between 1 and 1.38 instead of 0.75 calculated) and from the Esbiothrine/Bioallethrine relationship (ratio between 1.81 and 2.50 instead of 1.5 calculated) whatever may be the studied insect and the KT used as the reference ($KT_{50}$ or $KT_{90}$).

From this study, there is noted the existence of an interesting phenomena of synergistic insecticidal activity of the mixture of the invention of about 75% of S-Bioallethrine and about 25% of (R-Bioallethrine) Esbiothrine which is shown by relative power determination of Esbiothrine and Bioallethrine or Esbiothrine and S-Bioallethrine.

Various modifications of the compositions and methods of the invention may be made without departing from the spirit or scope thereof and it is to be understood that the invention is intended to be limited only as defined in the appended claims.

We claim:

1. An insecticidal composition comprising as the active ingredient an insecticidally effective amount of a synergistic mixture of 80 to 70% by weight of (S) 1-oxo-2-allyl-3-methylcyclopent-2-en-4-yl d trans chrysanthemate and 20 to 30% by weight of (R) 1-oxo-2-allyl-3-methyl-cyclopent-2-en-4-yl d trans chrysanthemate.

2. A composition of claim 1 wherein the mixture contains about 75% by weight of the (S) ester and about 25% by weight of the (R) ester.

3. A composition of claim 1 in the form of a fumigant.

4. A composition of claim 1 in the form of a combustible insecticidal coil.

5. A composition of claim 3 containing 0.03 to 1% by weight of the active ingredient.

6. A composition of claim 1 wherein an incombustible substrate is impregnated with the active ingredient.

7. A composition of claim 6 containing 0.03 to 95% by weight of the active ingredient.

8. A composition of claim 3 wherein the active ingredient is incorporated into a combustible oil.

9. A composition of claim 8 containing 0.03 to 95% by weight of the active ingredient.

10. A method of combatting insects comprising contacting said insects with a lethal amount of a composition of claim 1.

11. The method of claim 10 wherein the mixture contains 80 to 70% by weight of the (S) ester and 20 to 30% by weight of the (R) ester.

12. The method of claim 10 wherein the mixture contains about 75% by weight of the (S) ester and about 25% by weight of the (R) ester.

13. The method of claim 10 wherein the insects are sarcoptides or ixodides.

14. The method of claim 10 wherein the insects are ticks or scabies.

15. The method of claim 10 wherein the composition is vaporized by burning a combustible coil.

16. The method of claim 10 wherein the composition is vaporized by heating an incombustible substrate impregnated with the active ingredient.

17. The method of claim 10 wherein an oil containing the active ingredient is burned in a lamp provided with a wick.

* * * * *